United States Patent [19]
van Saarloos

[11] Patent Number: 5,418,582
[45] Date of Patent: May 23, 1995

[54] PHOTOKERATOSCOPE APPARATUS AND METHOD

[75] Inventor: Paul P. van Saarloos, Innaloo, Australia

[73] Assignee: Lions Eye Institute Perth, Nedlands, Australia

[21] Appl. No.: 137,708

[22] Filed: Oct. 15, 1993

[51] Int. Cl.$^6$ ............................................. A61B 3/10
[52] U.S. Cl. .................... 351/212; 351/211; 351/247
[58] Field of Search ................ 351/212, 211, 246, 247

[56] References Cited

U.S. PATENT DOCUMENTS

| | | | |
|---|---|---|---|
| 3,797,921 | 3/1974 | Kilmer et al. | 351/7 |
| 4,772,115 | 9/1988 | Gersten et al. | 351/212 |
| 4,863,260 | 9/1989 | Gersten et al. | 351/212 |
| 4,978,213 | 12/1990 | El Hage | 351/212 |

OTHER PUBLICATIONS van Saarloos, et al., "Improved Method for Calculation of Corneal Topography for Any Photokeratoscope Geometry", Optometry and Visio Science, vol. 68, No. 12, pp. 960–965.

*Primary Examiner*—William L. Sikes
*Assistant Examiner*—Hung Xuan Dang

[57] ABSTRACT

An improved photokeratoscopic method and apparatus for measuring corneal curvature and topography. The principal of parallax is used by generating a reference light point outside of the relevant plane of a ring generator, such that the relative apparent position of the reference light point with respect to the projected light rings provides a calibration reference that varies with distance of a cornea from the photokeratoscope. More particularly, the invention determines the coordinates in space and the tangent angle of the reflection point on the corneal surface of the image of the reference light point. This information defines the actual corneal topography at the reflection point, without making assumptions. These coordinates and tangent angle can be used to determine the actual distance d from the photokeratoscope lens to the apex of the cornea. An exact value of d permits better accuracy in calculating the central corneal radius of curvature and corneal topography. The present invention can be used with any known photokeratoscope geometry, including planar, spherical, or conical ring generators. The algorithm for computing d, and for calculating the central corneal radius of curvature and corneal topography, is shown in pseudocode, and may easily be implemented as a computer program.

26 Claims, 7 Drawing Sheets

PHOTOKERATOSCOPE APPARATUS AND METHOD

BACKGROUND OF THE INVENTION

1. Field of the Invention

This invention relates to ophthalmic instruments, and more particularly to an improved photokeratoscopic method and apparatus for measuring corneal curvature and topography.

2. Description of Related Art

In recent years, there has been increased interest in instruments that provide a quantitative measurement of corneal topography. This interest is due mainly to developments in surgical procedures that correct refractive errors through modification of the corneal shape. These procedures include radial keratotomy, epikeratophakia, and excimer laser keratectomy.

The most common method of assessing corneal topography is keratoscopy, which involves imaging a pattern of bright concentric circles of light (typically about 20) by reflection from the anterior surface of the cornea. The image of the circles may be interpreted qualitatively, with abnormalities in corneal shape producing a non-circular image. If the images are captured on film or by video imaging, the method is known as photokeratoscopy.

FIG. 1 diagrammatically shows a conventional photokeratoscope. An eye 1 is positioned external of an instrument which comprises (1) a ring generator 3, which may be planar, spherical, or conical, configured to project bright rings of known dimension upon the eye 1 when illuminated from the opposite side of the eye, (2) a light source 5, which is preferably toroidal so as to provide relatively uniform illumination behind the ring generator 3, (3) a lens group 7 for focusing the reflected images of the projected rings received from the eye, and (4) an imaging device 9 for capturing the focused image from the lens group 7. In most modern instruments, the imaging device 9 would digitize the focused image so as to provide a digital image that could be automatically evaluated or provide quantifiable information with the assistance of human intervention. The imaging device 9 may, for example, use a 512×512 pixel CCD device, which are commonly available from a number of commercial sources.

FIG. 2 is a close up of an eye 1 and a ring generator 3, showing that ribs or structures 11 around the ring generator (a cone in the example shown in FIG. 2) cause a series of bright light rings 13 to be projected onto the cornea of the eye 1.

Attempts have been made to quantitatively interpret photokeratoscopic images by digitizing the light ring images reflected from a cornea, and using selected equations implemented as computer programs to calculate corneal topography from the size and shape of the light ring images. However, exact calculation is not possible from photokeratoscope data, and many assumptions are made to obtain an estimate of the corneal topography.

A number of references have described such methods. One such reference is entitled "Improved Method for Calculation of Corneal Topography for any Photokeratoscope Geometry", by Paul P. van Saarloos and Ian J. Constable, *Optometry and Vision Science*, Vol. 68, No. 12, pp. 960–965, 1991, the teachings of which are hereby incorporated by reference. The van Saarloos reference teaches a mathematical method for estimating the central corneal radius of curvature and for calculating corneal topography from the radii of the rings in a photokeratoscope image.

FIGS. 3A and 3B are diagrams of the geometry of a conventional photokeratoscope in use with respect to a cornea C. The relevant angles and lengths are indicated, and have the meanings defined in the van Saarloos reference. The van Saarloos equations give a reasonably good approximation of the central corneal radius of curvature and corneal topography by using the measured radii of the rings in a photokeratoscope image and applying the known geometry of a photokeratoscope.

However, one problem with the van Saarloos method and other prior art methods is that, the distance d from the photokeratoscope lens to the apex of the cornea cannot be measured directly. The distance d is used in all equations to calculate corneal topography. Hence, an inaccurate value for d will affect the accuracy of all topographical calculations. The magnification (an hence angle $a_i$) is also highly dependent on the actual value of d.

The distance d can be approximated if the working distance wd (defined as the distance from the lens group 7 to the plane where an object would be perfectly focused onto the imaging device 9) and the photokeratoscope is focused perfectly. Put another way, d cannot be calculated accurately from wd if the photokeratoscope is not focused perfectly. Unfortunately, achieving perfect focus is often very difficult with present photokeratoscopes.

Accordingly, what is needed is a measurement of the distance d at the time a photokeratoscopic image is recorded. The present invention provides an improved apparatus and method for measuring d, which permits better accuracy than the prior art in calculating the central corneal radius of curvature and corneal topography.

SUMMARY OF THE INVENTION

The present invention is an improved photokeratoscopic method and apparatus for measuring corneal curvature and topography. The principal of parallax is used by generating a reference light point outside of the relevant plane of a ring generator, such that the relative apparent position of the reference light point with respect to the projected light rings provides a calibration reference that varies with distance of a cornea from the photokeratoscope. More particularly, the invention determines the coordinates in space and the tangent angle of the reflection point on the corneal surface of the image of the reference light point. This information defines the actual corneal topography at the reflection point, without the assumptions made by prior art techniques. These coordinates and tangent angle can be used to determine the actual distance d from the photokeratoscope lens to the apex of the cornea. An exact value of d permits better accuracy than the prior art in calculating the central corneal radius of curvature and corneal topography.

The present invention can be used with any known photokeratoscope geometry, including planar, spherical, or conical ring generators. The algorithm for computing d, and for calculating the central corneal radius of curvature and corneal topography, is shown in pseudocode, and may easily be implemented as a computer program.

The details of the preferred embodiment of the present invention are set forth in the accompanying drawings and the description below. Once the details of the invention are known, numerous additional innovations and changes will become obvious to one skilled in the art.

BRIEF DESCRIPTION OF THE DRAWINGS

Like reference numbers and designations in the various drawings refer to like elements.

DETAILED DESCRIPTION OF THE INVENTION

Throughout this description, the preferred embodiment and examples shown should be considered as exemplars, rather than as limitations on the present invention.

Figure 4A:
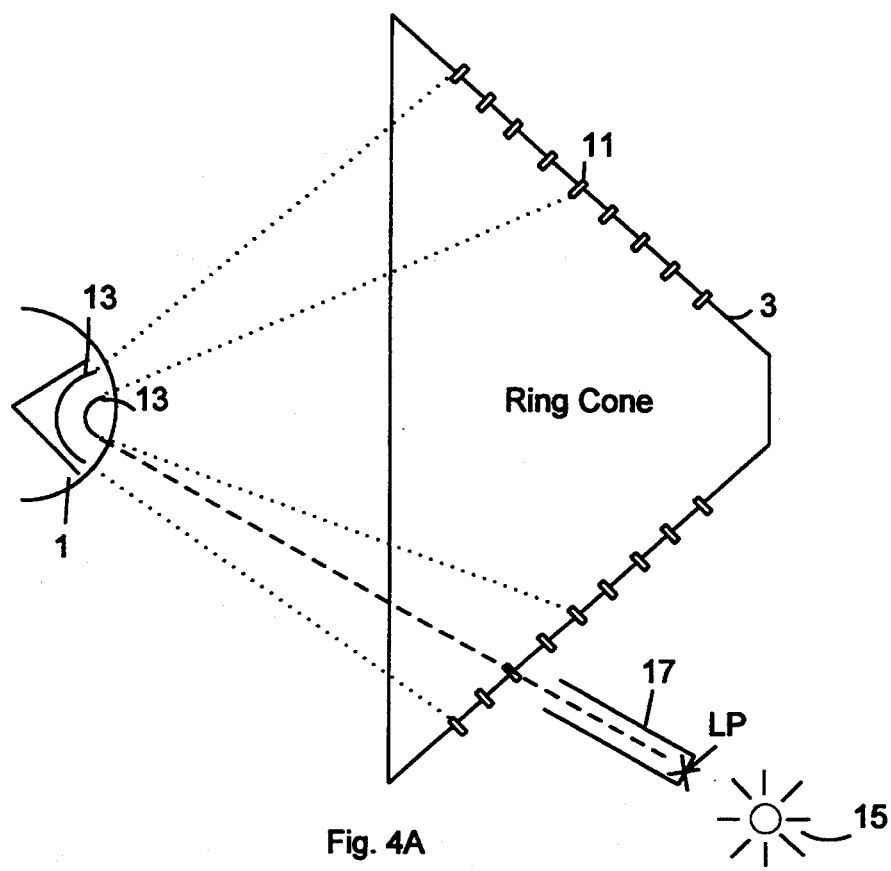
FIG. 4A is a cross-sectional side view block diagram of a preferred embodiment of the present invention.

FIG. 4A is a cross-sectional side view block diagram of a preferred embodiment of the present invention. FIG. 4A shows a close up of an eye 1 and a ring generator 3, showing that ribs or structures 11 around the ring generator (a cone, in this example) cause a series of bright light rings 13 to be projected onto the cornea of the eye 1. The ring generator 3 is also known as a "faceplate".

In addition, a reference light point LP is positioned spaced from the faceplate relative to the eye. In the preferred embodiment, the reference light point LP is generated by placing a light source 15 behind a small, hollow shield tube 17 having a pinhole in the end adjacent the light source 15. The other end of the tube 17 is aimed at the expected position of a target cornea 1. The effect of this arrangement is to create a point source behind the plane of the ring cone faceplate (for spherical and conical faceplates, "plane" means the local tangent plane adjacent to the reference light point LP along the line from the cornea to the reference light point LP).

Figure 4B:
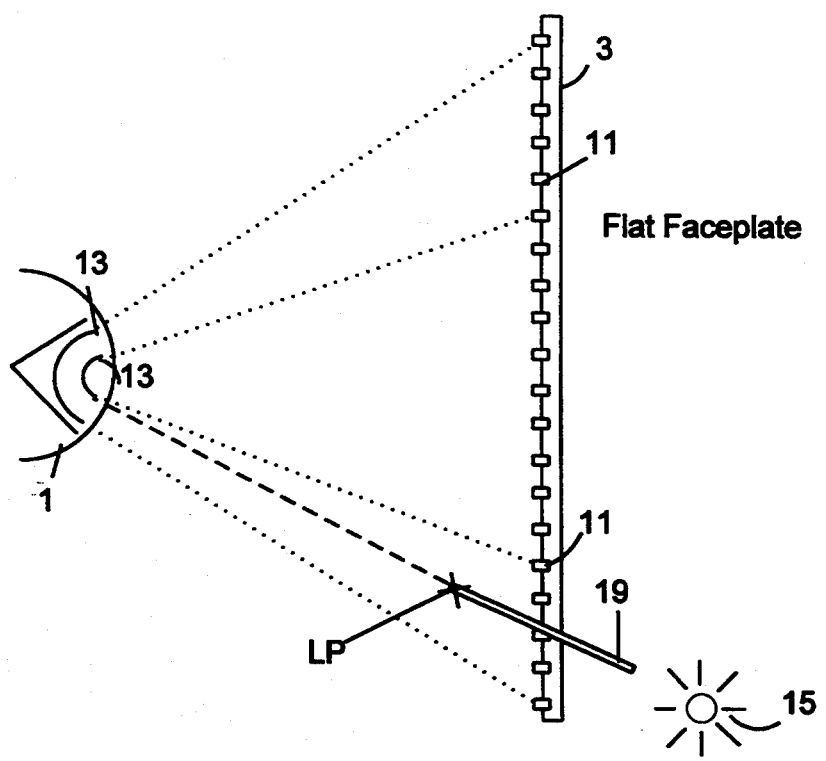
FIG. 4B is a cross-sectional side view block diagram of an alternative embodiment of the present invention.

FIG. 4B is a cross-sectional side view block diagram of an alternative embodiment of the present invention. In this embodiment, a flat faceplate is used as the ring generator 3, showing that the present invention can be used with other photokeratoscope geometries. Also, instead of the reference light point LP being placed behind the ring generator 3 with respect to the cornea, the reference light point LP is positioned in front of the ring generator 3. This may be accomplished, for example, by use of a light pipe 19 situated to guide light from a light source 15 to a tip on the corneal side of the faceplate. The effect of this arrangement is to create a point source in front of the plane of the faceplate (again, for spherical and conical faceplates, "plane" means the local tangent plane adjacent to the reference light point LP along the line from the cornea to the reference light point LP).

While a single reference light point LP is described, the invention extends to equivalent structures. For example, more than one reference light point LP may be employed by using multiple tubes 17 or light pipes 19. Alternatively, a complete or partial ring (for example, of light conducting plastic) may be used with a suitable light source 15, such as a toroidal fluorescent light, so long as the light emitting surface of the ring is not in the plane of the faceplate at any local tangent. Further, the combination of a tube 17 or light pipe 19 and a light source 15 can be replaced by a unitary device, such as a low-power integrated circuit laser or light emitting diode.

Whatever the form of the reference light point LP, it is important to know the position of the reference light point LP relative to a reference plane (such as the photokeratoscope lens, although other reference planes could be used), as is more fully explained below.

Figure 5A:
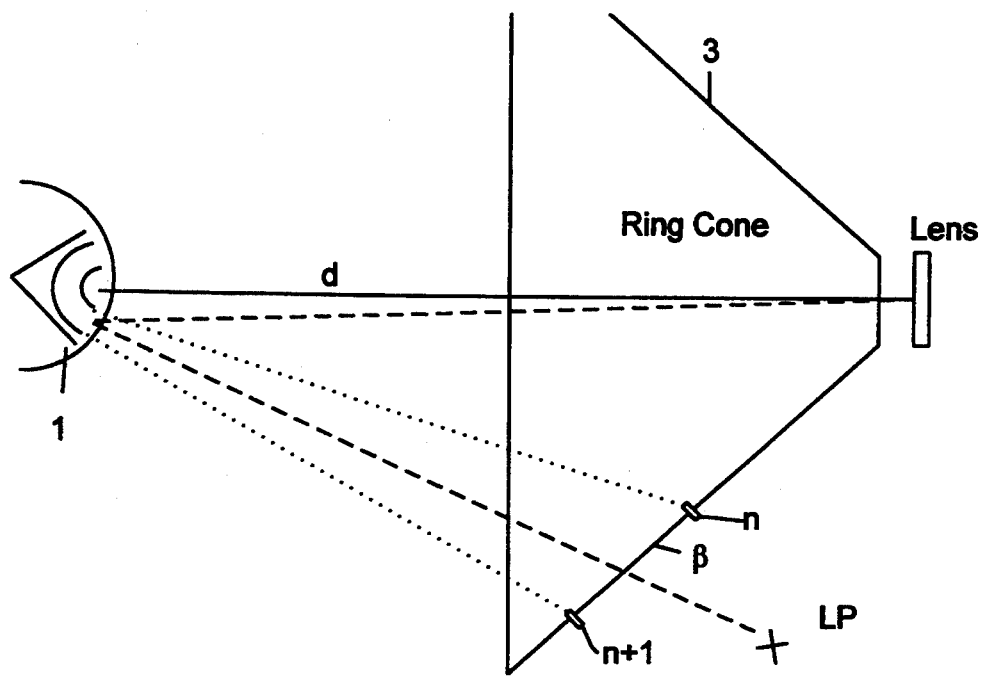
FIG. 5A is a diagram showing the position of a reference light point, generated in accordance with the present invention, to a pair of projected photokeratoscope light rings, when a photokeratoscope is positioned at a first distance from a cornea.
Figure 5B:
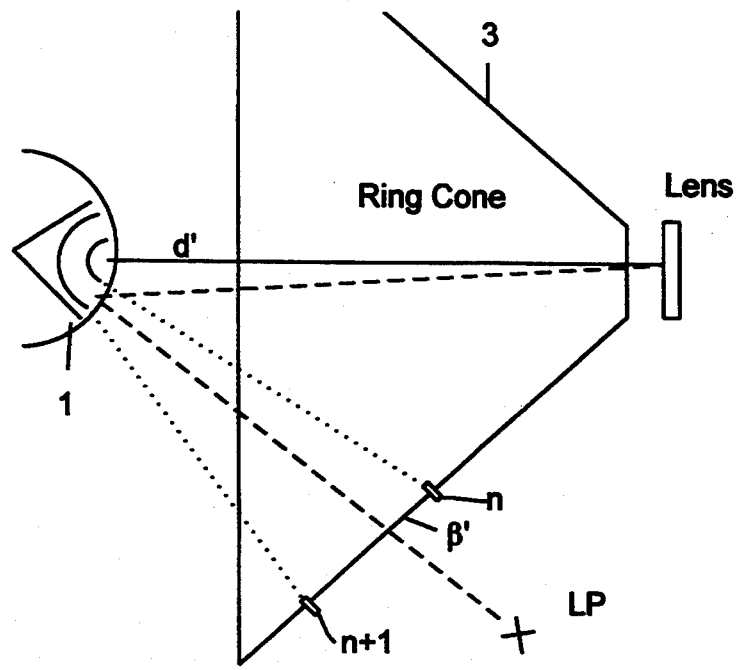
FIG. 5B is a diagram showing the position of a reference light point, generated in accordance with the present invention, to a pair of projected photokeratoscope light rings, when a photokeratoscope is positioned at a second distance from a cornea.

FIG. 5A is a diagram showing the position of a reference light point LP, generated in accordance with the present invention, to a pair of projected photokeratoscope light rings n and n+1, when a photokeratoscope is positioned at a first distance from a cornea. FIG. 5B is a diagram showing the position of a reference light point LP, generated in accordance with the present invention, to a pair of projected photokeratoscope light rings n and n+1, when a photokeratoscope is positioned at a second distance from a cornea. It can be seen from these two drawings that the apparent position of the reference light point LP relative to the adjacent light rings n and n+1 changes as a function of the distance d, d' of the photokeratoscope to the cornea of the eye 1.

Figure 1:
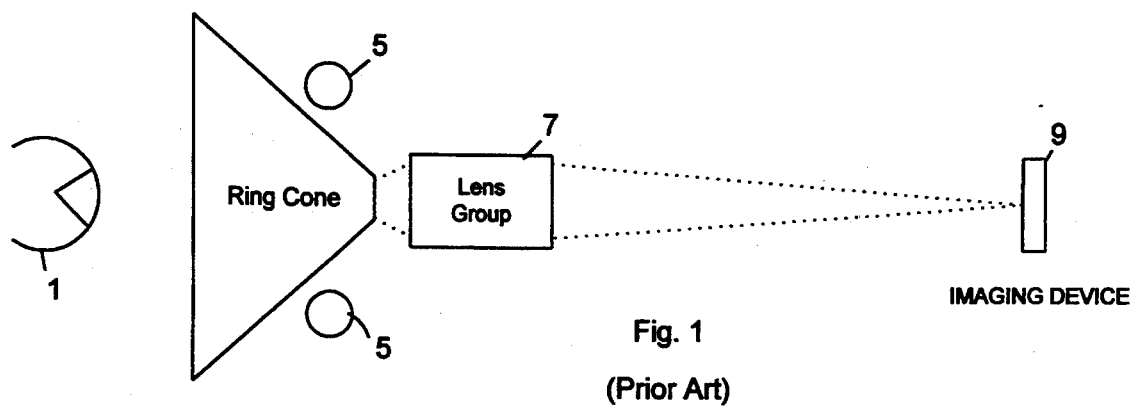
FIG. 1 is cross-sectional side view block diagram of a prior art photokeratographic instrument.
Figure 2:
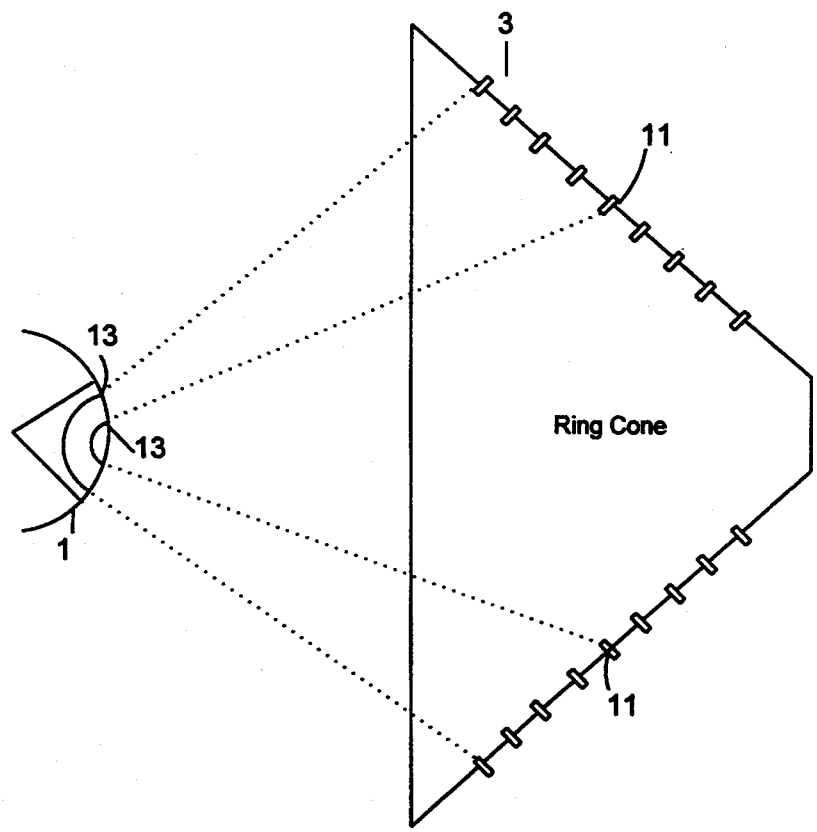
FIG. 2 is an enlarged view of part of FIG. 1, showing light rings projected onto an eye.
Figure 6:
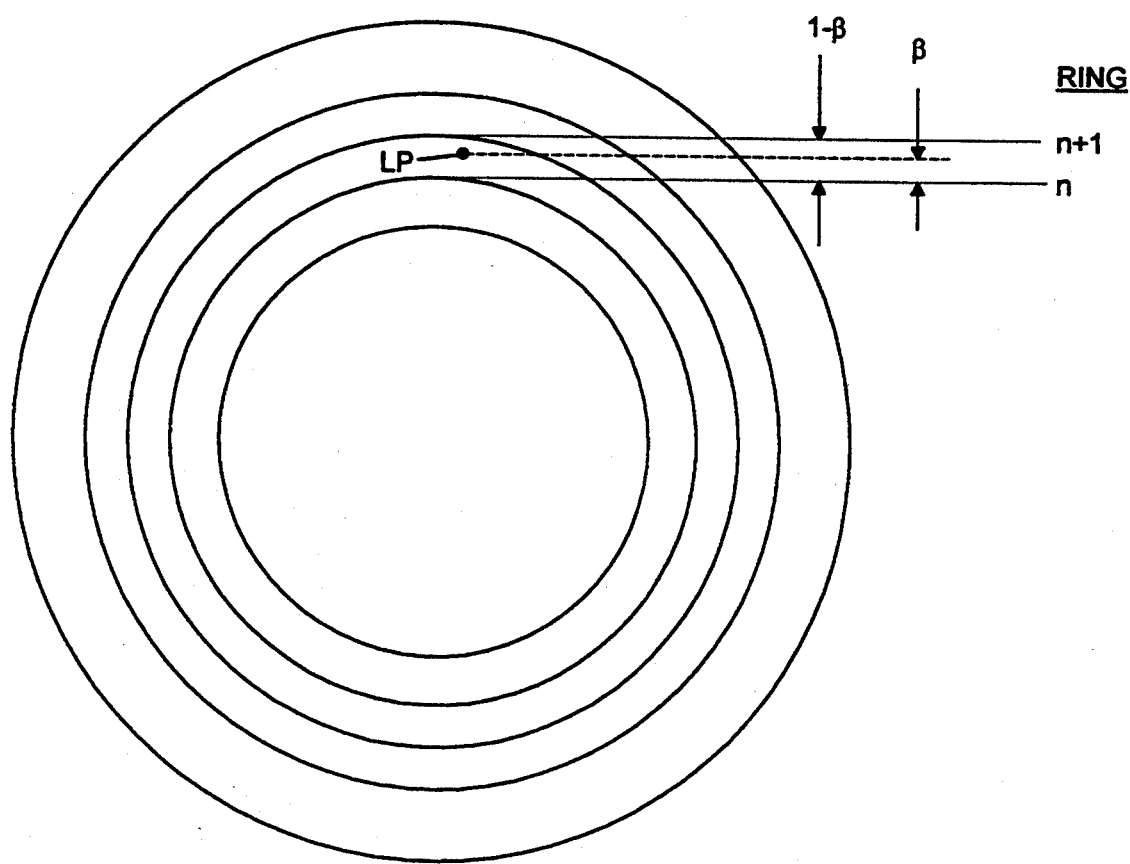
FIG. 6 is a diagram showing the relative position of a reference light point, generated in accordance with the present invention, to a pair of projected photokeratoscope light rings.

FIG. 6 is a diagram showing the relative position of a reference light point LP, generated in accordance with the present invention, to a pair of projected photokeratoscope light rings, n and n+1. (This is the view of the projected rings as seen by the imaging device 9 in FIG. 1). The ratio of the distance of the reference light point LP to ring n, relative to the distance of ring n to ring n+1 (taken here as unity), defines a value $\beta$. The value of $\beta$ will change depending on the distance of the photokeratoscope from the cornea. This phenomenon, due to parallax, permits definition of a measurement geometry of the photokeratoscope from which a direct measurement can be made of the distance d. From this measurement, more accurate computations can be made of the central corneal radius of curvature and corneal topography.

Computation of the value $\beta$ can be made automatically or manually, using the following algorithm, presented as pseudocode:

Calculation of tangent point for Light Point

Find rings on image.
Find image of reference light point LP.
Determine which rings the reference light point LP falls between. These rings are referred to as n and n+1.
Calculate $\beta$ as the ratio of the distances between the reference light point LP and rings n and n+1.

Calculation of Reference Light Point Image Coordinates & Tangent

Figure 7:
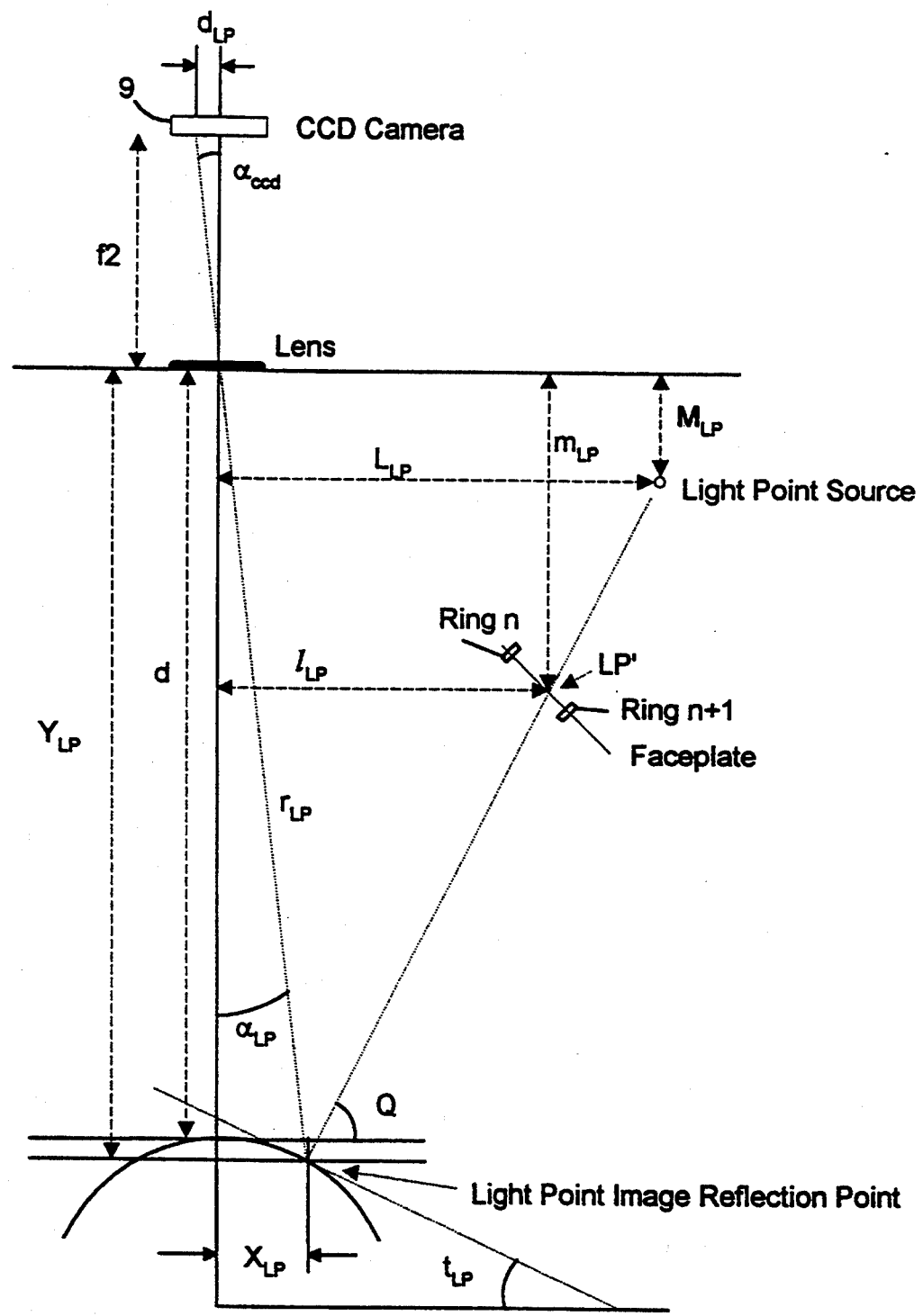
FIG. 7 is a diagram of a photokeratoscope in accordance with the present invention, showing the geometry for calculating the central corneal radius of curvature and corneal topography.

FIG. 7 is a diagram of a photokeratoscope in accordance with the present invention, showing the geometry for calculating the central corneal radius of curvature and corneal topography using a reference light point LP. The following variables are used in the computations discussed below:

LP' The apparent position of the reference light point LP in the plane of the ring faceplate $m_{LP}$ The distance (or coordinate value) from the lens to the apparent position LP' of the reference light point LP in the plane of the ring faceplate $l_{LP}$ The distance (or coordinate value) from the optical axis of the lens to the apparent position LP' of the reference light point LP in the plane of the ring faceplate $M_{Lp}$ The distance (or coordinate value) from the lens to the reference light point LP $L_{LP}$ The distance (or coordinate value) from the optical axis of the lens to the reference light point LP $Y_{LP}$ The distance (or coordinate value) from the lens to the image of the reference light point LP reflected from the cornea $X_{LP}$ The distance (or coordinate value) from the optical axis of the lens to the image of the reference light point LP reflected from the cornea $t_{LP}$ The angle (preferably in radians) of the tangent line to the image of the reference light point LP reflected from the cornea Q The angle that a line connecting the reference light point LP to the recollection point makes with a line perpendicular to the optical axis of the lens f2 The distance from the secondary principal plane of the lens to the imaging device 9 (e.g., a CCD camera)

Other variables are evident from FIG. 7.

Using the additional geometric information provided by the reference light point LP, $X_{LP}$, $Y_{LP}$, and $t_{LP}$ can be calculated from the geometry shown in FIG. 7 as follows:

(1) $l_{LP}=\beta \cdot (l_{n+1}-l_n)+l_n$
(2) $m_{LP}=\beta \cdot (m_{n+1}-m_n)+m_n$
(3) $\tan Q=(M_{LP}-m_{LP})/(l_{LP}-L_{LP})$
(4) $\alpha_{ccd}=\tan^{-1}(d_{LP}/f2)$
(5) $Y_{LP}=(M_{LP}+L_{LP}\tan Q)/(1+(\tan \alpha_{LP})\cdot(\tan Q)$
(6) $X_{LP}=Y_{LP}\tan \alpha_{LP}$
(7) $t_{LP}=(\pi/2-\alpha_{LP}-Q)/2$ Thus, the invention determines the coordinates in space ($X_{LP}$, $Y_{LP}$) and the tangent angle ($t_{LP}$) of the reflection point on the corneal surface of the image of the reference light point. This information defines the actual corneal topography at that reflection point, without the assumptions made by prior art techniques, as described in the van Saarloos reference.

With these values, significantly more accurate calculations of corneal radius of curvature and corneal topography can be made in comparison to the prior art. To do so, the equations from the van Saarloos reference must be altered in part. Because an iterative process must still be used, following is a "pseudocode" explanation of the mathematical formulas and control structures that best explain the preferred embodiment of the present invention. One of ordinary skill in the art could easily program such pseudocode using a desired computer language.

Calculation of Central Corneal Radius of Curvature

Relating the shape of the cornea at the position where one ring is reflected to the shape of the cornea where an adjacent ring is reflected requires an iterative computation. A value $\overline{Y}_0$ for the curvature at the center of the cornea is needed to initiate this calculation.

Figure 3A:
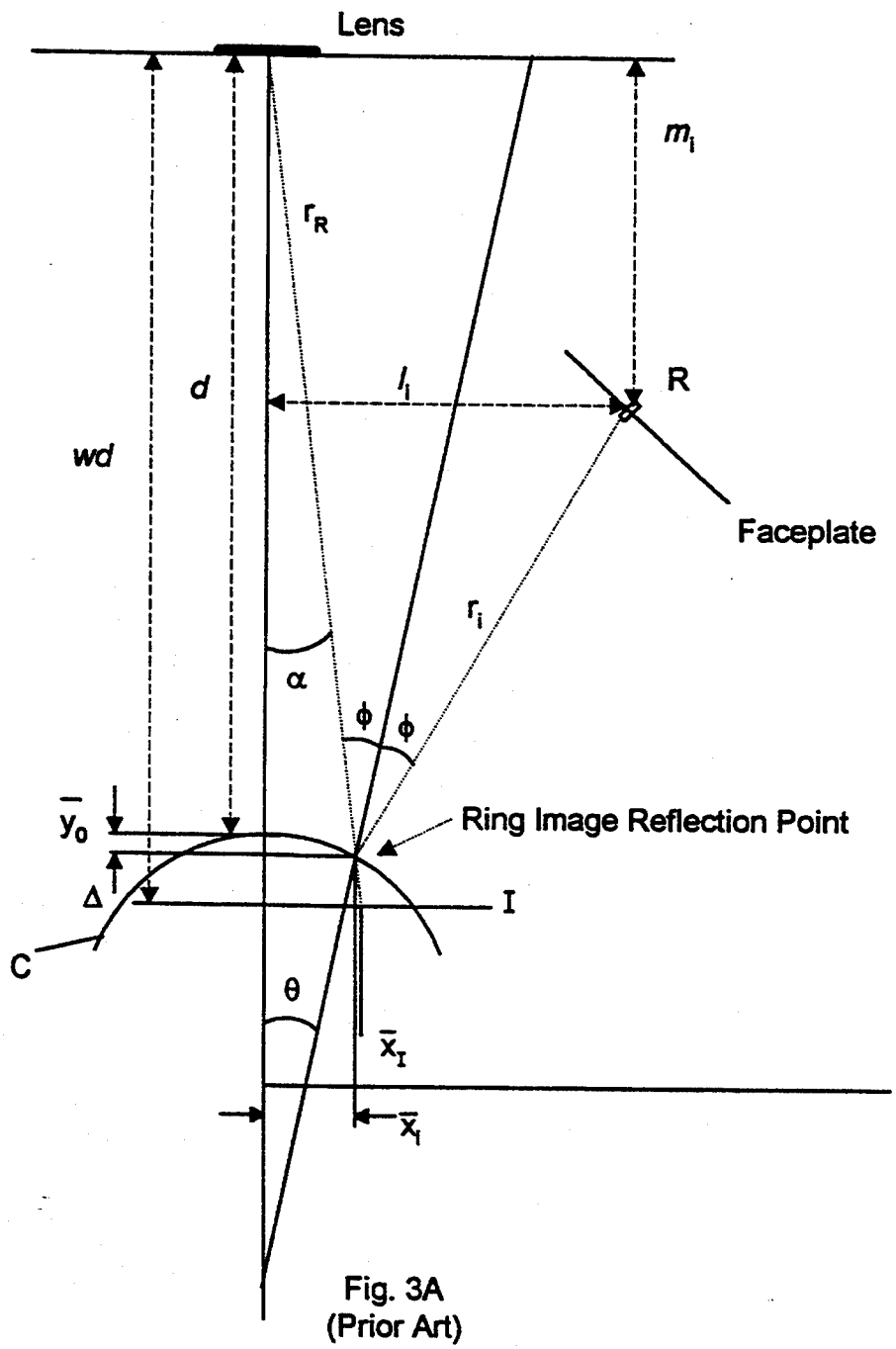
FIG. 3A is a diagram showing the geometry of a prior art photokeratoscope for calculating the central corneal radius of curvature.
Figure 3B:
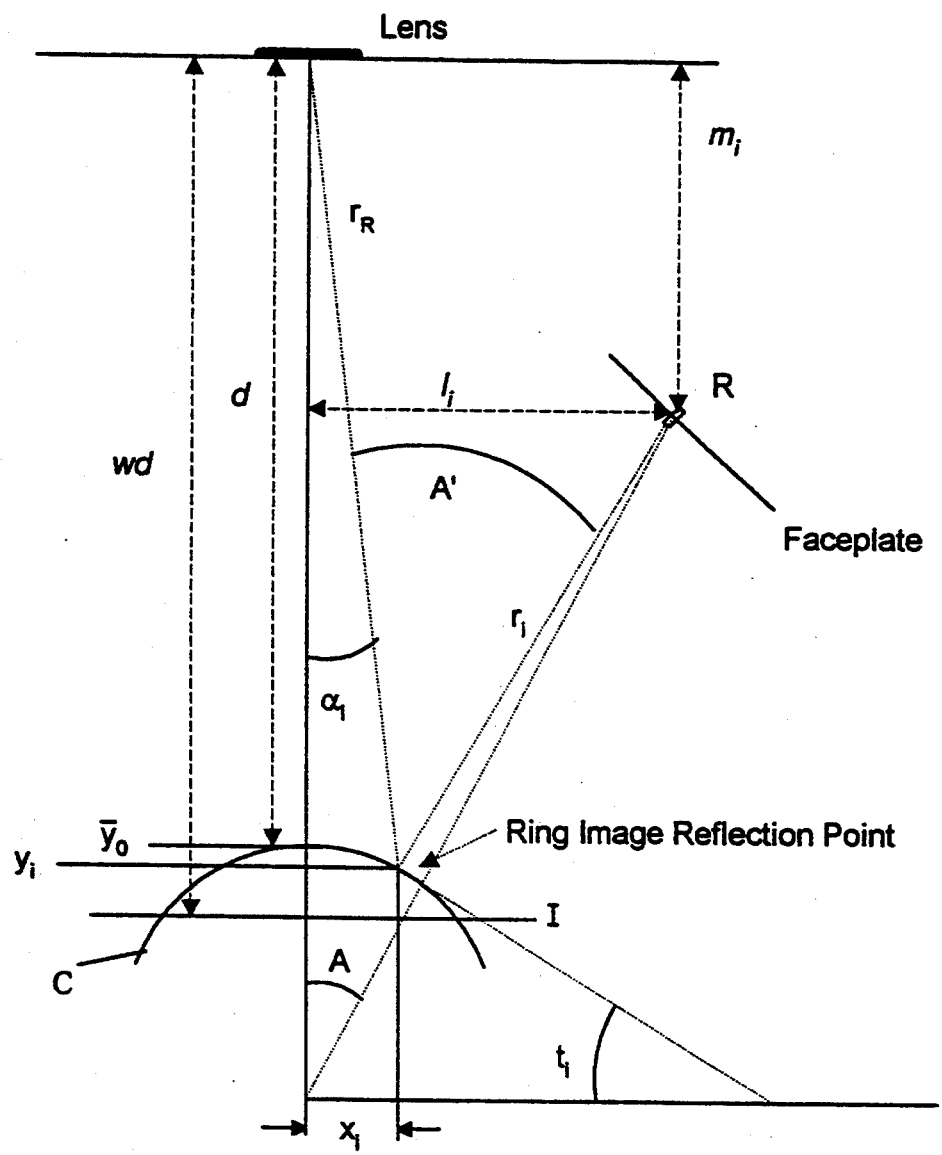
FIG. 3B is a diagram showing the geometry of a prior art photokeratoscope for calculating corneal topography.

The value used for $\overline{Y}_0$ could be assumed to be an average value (i.e., 7.8 mm), or a keratometry reading could be used. The keratometry reading is generally an average curvature over a 3 to 4 mm meridional arc of the cornea surface. However, this does not provide an accurate measure of the central curvature. Assuming a photokeratoscope image is in proper focus, a measure of the central corneal curvature can be obtained from the average radius of the inner ring image, as is taught in the van Saarloos reference. However, using the added information provided by the presence of the reference light point LP, the invention provides an improved algorithm for calculating the central corneal radius of curvature. Following is pseudocode for the improved algorithm:

(Notes: Origin is shifted to the optics primal plane, and all Y values are relative to this origin. R refers to the $i^{th}$ keratoscope ring. $r_R$ is the distance from the lens to the corneal reflection point for the image of a ring R, as is shown in FIG. 3B. $r_i$ is the distance from such a corneal reflection point to the corresponding ring R on the faceplate, as is shown in FIG. 3B. Equation numbers on the right side denote correspondence to, or, if primed, substitutions for, similarly numbered equations in the van Saarloos reference.)

Back propagate original van Saarloos algorithm along the meridian for the reference light point LP. Use double iterative loop to solve for $X_{i-1}$, $Y_{i-1}$, and $t_{i-1}$ as follows:

```
IF (r ≤ 0.25) THEN
    StartRing = n−1
ELSE
    StartRing = n
ENDIF
X_i = X_LP
Y_i = Y_LP                          {starting values derived above}
t_i = t_LP
X_{i−1} = X_LP · (n − 1)/(n − r)    {first estimate of X_{i−1}}
FOR (i = StartRing to 1)
```

-continued

```
    α_ccd = tan^-1(d_i/f2)         {d_i is same as d_LP, but for i^th ring}
    α_i = α_ccd
ENDFOR
FOR (i = StartRing to 1)
                                    {1st estimate of t_{i-1}}
                                    {l_i, m_i equivalent to l_LP, m_LP, but for i^th ring}
    A = α_i + arctan ((l_i − X_i)/(Y_i − m_i))
    t_{i-1} = A/2
    WHILE (TRUE)                   {outer Y_{i-1} convergence loop}
        Y_{i-1} = Y_i − (X_{i-1} − X_i)(cos t_{i-1} − cos t_i)/(sin t_{i-1} − sin t_i)        (9)
        IF (Y_{i-1} converged from last outer loop value) THEN
            BREAK
        ENDIF
        WHILE (TRUE)               {inner Y_{i-1} convergence loop}
            r_i^2 = (l_{i-1} − X_{i-1})^2 + (Y_{i-1} − m_{i-1})^2                            (10')
            r_R^2 = (X_{i-1})^2 + (Y_{i-1})^2                                                (11')
            A' = cos^-1((l_{i-1}^2 + m_{i-1}^2 − r_R^2 − r_i^2)/(−2r_R r_i))                 (12')
            t_{i-1} = (π/2) − (A'/2) − tan^-1((Y_{i-1} − m_{i-1})/(l_{i-1} − X_{i-1}))       (13')
            Y_{i-1} = Y_i − (X_{i-1} − X_i)(cos t_{i-1} − cos)/(sin t_{i-1} − sin t_i)       (9)
            IF (Y_{i-1} converged from last value) THEN
                BREAK
            ENDIF
        ENDWHILE                   {end inner Y_{i-1} convergence loop}
        X_{i-1} = r_R · sin α_{i-1}                                                          (14)
    ENDWHILE                       {end outer Y_{i-1} convergence loop}
    IF (ring > 1) THEN
        X_i = X_{i-1}              {starting conditions for next ring}
        Y_i = Y_{i-1}
        t_i = t_{i-1}
        X_{i-1} = X_i · ((α_{i-1})/(α_i))   {starting estimate of X_{i-1}}
    ENDIF
ENDFOR                             {end of FOR loop over rings}
Since X_0 and t_0 = 0, Y_0 can be determined from a simplified Equation (9). Note that
d = Y_0
    d = Y_1 + ((X_1)(1 − cos t_1))/sin t_1
    Ȳ_0 = X_i/sin(t_i)
Ȳ_0 may also be computed using Equation (9).
```

Calculation of Corneal Shape

As is known, there is no exact solution to calculating corneal topography from the radii of the rings in a photokeratoscope image. However, the elevation and surface tangent angle of the cornea at one point on one of the photokeratoscope ring images to the same values at a point on the same radius on an adjacent ring can be used to approximate the corneal topography.

This approximation assumes that the cornea is a regular curved surface and is independent of the photokeratoscope geometry. Because prior art equations for such an approximation have 3 unknowns and hence cannot be solved directly, it is known to solve such equations iteratively. However, to solve such equations iteratively, the topography at some point of the cornea must be known to initiate the calculations. Accordingly, the information used to calculate the central corneal radius of curvature, described above, can be used to provide initial data points, along with information derived from the known geometry of the photokeratoscope.

Corneal topography can be plotted in three dimensions or the shape through any cross section can be plotted. The preferred technique is to calculate the focusing or refractive power of the cornea using the local curvature. Equations (15) and (16) set forth below provide the information necessary for such a plot. $K_L$ is the Local Refractive Power in diopters when $r_L$ is expressed in meters, and have the same meaning as in the van Saarloos reference.

Following is pseudocode for determining corneal topography, and plotting such information against a standard radius.

```
(Note: Origin is now back at center of cornea, and all Y values are relative to this origin.)
d_0 = d + Ȳ_0                     {starting values derived above}
X_0 = 0
Y_0 = Ȳ_0
t_0 = 0
wd = d + 1/[(1/(d − m_i)) + (2/Ȳ_0)]   {only needed to set starting estimate for X_i}
X_i = ½(wd + d_0 − Ȳ_0) tan α_i       {get starting estimate for X_i}
FOR (i = 1 to MaxRings)
    α_i = tan^1 (d_i/f2)
    A = arctan (l_i/(d_0 − m_i))
    t_i = A/2
    WHILE (TRUE)                  {outer Y_i convergence loop}
        Y_i = Y_{i-1} − ((X_{i-1} − X_i)(cos t_{i-1} − cos t_i))/(sin t_{i-1} − sin t_i)     (9)
        IF (Y_i converged from last value) THEN
            BREAK
        ENDIF
        WHILE (TRUE)              {inner Y_i convergence loop}
            r_i^2 = (l_i − X_i)^2 + (d_0 − Y_i − m_i)^2                                     (10)
            r_R^2 = (X_i)^2 + (d_0 − Y_i)^2                                                 (11)
            A' = cos^-1(l_i^2 + m_i^2 − r_R^2 − r_i^2)/(−2r_R r_i)                          (12)
```

-continued $$t_i = (\pi/2) - (A'/2) - \tan^{-1}((d_0 - Y_i - m_i)/(l_i - X_i)) \quad (13)$$
$$Y_i = Y_{i-1} - ((X_{i-1} - X_i)(\cos t_{i-1} - \cos t_i))/(\sin t_{i-1} - \sin t_i) \quad (9)$$
```
            IF (Y_i converged from last outer loop value) THEN
                BREAK
            ENDIF
        ENDWHILE                          {end inner Y_i convergence loop}
        X_i = r_R · sin α_i                                                   (14)
    ENDWHILE                              {end outer Y_i convergence loop}
    r_L = X_i/sin t_i                                                         (15)
    K_L = 0.3375/r_L                                                          (16)
    X_{i-1} = X_i                         {initialize for next ring}
    Y_{i-1} = Y_i
    t_{i-1} = t_i
                                          {get estimate for X_i for next ring}
    X_i = ½(wd + d_0 - Y_{i-1}) · tan α_i
ENDFOR                                    {end of FOR loop over rings}
```

The equations presented above enhance the accuracy of calculating corneal topography from photokeratoscope results, for any corneal shape, with only a small increase in computation time and no increase in the sensitivity to errors. They also apply to any photokeratoscope geometry, and they are easily implemented in a computer program. One of ordinary skill in the art could program such equations and program control structures using a desired computer language, such as C, PASCAL, FORTRAN, or BASIC.

In summary, the present invention uses the principal of parallax by generating a reference light point outside of the relevant plane of a ring generator, such that the relative apparent position of the reference light point with respect to the projected light rings provides a calibration reference that varies with distance of a cornea from the photokeratoscope. More particularly, the invention determines the spatial coordinates and the tangent angle of the reflection point on the corneal surface of the image of the reference light point. This information defines the actual corneal topography at the reflection point, without the assumptions made by prior art techniques. These coordinates and tangent angle can be used to determine the actual distance d from the photokeratoscope lens to the apex of the cornea. An exact value of d permits better accuracy than the prior art in calculating the central corneal radius of curvature and corneal topography.

A number of embodiments of the present invention have been described. Nevertheless, it will be understood that various modifications may be made without departing from the spirit and scope of the invention. For example, although the distance d has been defined as the distance from the photokeratoscope lens to the apex of the cornea, other reference points or plans in the photokeratoscope could be used, so long as their relative position with respect to the reference light point LP is known. Accordingly, it is to be understood that the invention is not to be limited by the specific illustrated embodiment, but only by the scope of the appended claims.

I claim:

1. A method for measuring the distance from a target cornea to a reference point of a photokeratoscope having a ring generator, comprising the steps of:
   (a) providing a reference light point outside of the local tangent plane of the ring generator;
   (b) imaging a reflection point of the reference light point from the target cornea;
   (c) computing spatial coordinates and a tangent angle of the reflection point of the reference light point from the target cornea from the imaged reflection point; and
   (d) computing the distance from the target cornea to the reference point of the photokeratoscope based upon the computed spatial coordinates and the computed tangent angle.

2. The method defined by claim 1, wherein the spatial coordinates of the reflection point of the reference light point from the target cornea are represented by Cartesian coordinates $X_{LP}$ and $Y_{LP}$, and wherein the tangent angle of the reflection point of the reference light point from the target cornea is represented by an angle $t_{LP}$, further including the step of computing $X_{LP}$, $Y_{LP}$, and $t_{LP}$ according to the following formulae:

$$Y_{LP} = (M_{LP} + L_{LP} \tan Q)/(1 + (\tan \alpha_{LP}) \cdot (\tan Q))$$

$$X_{LP} = Y_{LP} \tan \alpha_{LP}$$

$$t_{LP} = (\pi/2 - \alpha_{LP} - Q)/2$$

wherein $M_{LP}$ is the distance from a lens of the photokeratoscope to the reference light point,
$L_{LP}$ is the distance from an optical axis of the lens to the reference light point,
Q is an angle that a line connecting the reference light point to the reflection point makes with respect to a line perpendicular to the optical axis of the lens, and
$\alpha_{LP}$ is an angle that a line connecting the lens to the reflection point of the reference light point from the target cornea makes with respect to the optical axis of the lens.

3. The method defined by claim 1, wherein the ring generator is a planar faceplate.

4. The method defined by claim 1, wherein the ring generator is a spherical faceplate.

5. The method defined by claim 1, wherein the ring generator is a conical faceplate.

6. The method defined by claim 1, wherein the ring generator includes a partial ring made of light-conducting material and a light source.

7. The method defined by claim 1, wherein the reference light point is provided by positioning a light source behind a light pipe, wherein the light pipe has an opening in a first end positioned adjacent the light source, and wherein the light pipe has a second end aimed at the target cornea.

8. The method defined by claim 7, wherein the light source is a low-power laser.

9. The method defined by claim 7, wherein the light source is a light emitting diode.

10. The method defined by claim 7, wherein the light pipe is a fiber optic.

11. The method defined by claim 1, wherein the reference light point is positioned in front of the local tangent plane of the ring generator, such that the reference light point is in closer proximity to the target cornea than is the ring generator.

12. The method defined by claim 1, wherein the reference light point is positioned behind the local tangent plane of the ring generator, such that the ring generator is in closer proximity to the target cornea than is the reference light point.

13. An improved method for computing the central corneal radius of curvature of a target cornea, comprising the steps of:
(a) providing a photokeratoscope having a ring generator which projects a plurality of light rings onto the target cornea;
(b) providing a reference light point outside of the local tangent plane of the ring generator;
(c) imaging the plurality of light rings reflected from the target cornea;
(d) imaging a reflection point of the reference light point from the target cornea;
(e) selecting two imaged light rings, n and n+1, wherein the imaged reflection point falls between the imaged light rings n and n+1;
(f) calculating a ratio of distances $\beta$ between the imaged light rings n and n+1 and the imaged reflection point;
(g) defining a measurement geometry of the photokeratoscope based upon the calculated ratio $\beta$; and
(h) computing the central corneal radius of curvature of the target cornea based upon the defined measurement geometry.

14. The improved method of claim 13, wherein the central corneal radius of curvature of the target cornea is computed in an iterative manner.

15. An improved method for approximating the topography of a target cornea, comprising the steps of:
(a) providing a photokeratoscope having a ring generator which projects a plurality of light rings onto the target cornea;
(b) providing a reference light point outside of the local tangent plane of the ring generator;
(c) imaging the plurality of light rings reflected from the target cornea;
(d) imaging a reflection point of the reference light point from the target cornea;
(e) selecting two imaged light rings, n and n+1, wherein the imaged reflection point falls between the imaged light rings n and n+1;
(f) calculating a ratio of distances $\beta$ between the imaged light rings n and n+1 and the imaged reflection point;
(g) defining a measurement geometry of the photokeratoscope based upon the calculated ratio $\beta$; and
(h) approximating the topography of the target cornea based upon the defined measurement geometry.

16. An improved photokeratoscopic apparatus, comprising:
(a) a ring generator, having a plurality of structures for projecting a plurality of rings onto a target cornea;
(b) a reference light source positioned outside of the local tangent plane of the ring generator, for projecting light from the reference light source onto the target cornea;
(c) an imaging system, positioned adjacent the ring generator, such that the imaging system captures images of the projected rings reflected from the target cornea and an image of the reference light source reflected from the target cornea; and
(d) means for determining a relative position of the image of the reference light source with respect to images of at least two of the projected rings to provide a calibration reference that varies with distance of the target cornea from the photokeratoscope.

17. The improved photokeratoscopic apparatus of claim 16, wherein the ring generator is a planar faceplate.

18. The improved photokeratoscopic apparatus of claim 16, wherein the ring generator is a spherical faceplate.

19. The improved photokeratoscopic apparatus of claim 16, wherein the ring generator is a conical faceplate.

20. The improved photokeratoscopic apparatus of claim 16, wherein the ring generator includes a partial ring made of light-conducting material and a light source.

21. The improved photokeratoscope apparatus of claim 16, wherein the reference light source comprises a light source and a light pipe, and wherein the light source is positioned behind the light pipe, and wherein the light pipe has an opening in a first end positioned adjacent the light source, and wherein the light pipe has a second end aimed at the target cornea.

22. The improved photokeratoscopic apparatus of claim 21, wherein the light source is a low-power laser.

23. The improved photokeratoscopic apparatus of claim 21, wherein the light source is a light emitting diode.

24. The improved photokeratoscopic apparatus of claim 21, wherein the light pipe is a fiber optic.

25. The improved photokeratoscope apparatus of claim 16, wherein the reference light source is positioned in front of the local tangent plane of the ring generator, such that the reference light source is in closer proximity to the target cornea than is the ring generator.

26. The improved photokeratoscope apparatus of claim 16, wherein the reference light source is positioned behind the local tangent plane of the ring generator, such that the ring generator is in closer proximity to the target cornea than is the reference light source.

* * * * *